United States Patent [19]

Bergson

[11] 4,210,508
[45] Jul. 1, 1980

[54] ELECTROLYTIC HYGROMETER IMPROVEMENT

[76] Inventor: Gustav Bergson, Cedarbrook Hill Apts., Apt. B-117, Wyncote, Pa. 19095

[21] Appl. No.: 640,818

[22] Filed: Dec. 15, 1975

[51] Int. Cl.² .......................................... G01N 27/46
[52] U.S. Cl. ............................................. 204/195 W
[58] Field of Search ............... 204/195 W, 336.5, 292, 204/290 F, 195 R

[56] References Cited

U.S. PATENT DOCUMENTS

| | | | |
|---|---|---|---|
| 1,477,099 | 12/1923 | Baum | 204/290 F |
| 2,830,945 | 4/1958 | Keidel | 204/195 W |

*Primary Examiner*—G. L. Kaplan
*Attorney, Agent, or Firm*—Eugene Chovanes; Edward Lovett Jackson

[57] ABSTRACT

In the present invention the cell of the electrolytic hygrometer is fabricated with a helical pair of different wires which may be either two precious metals or one of these with one non-precious metal. Appropriate polarities are included.

6 Claims, 5 Drawing Figures

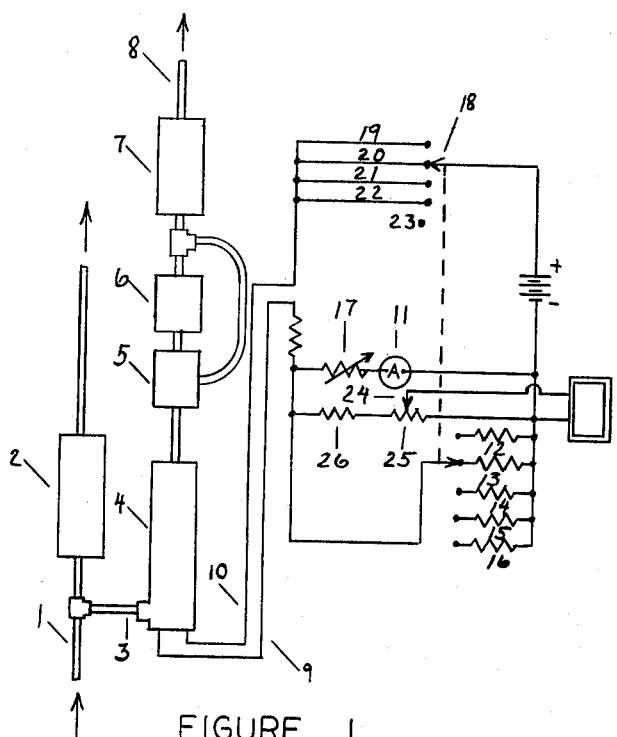
FIGURE 1
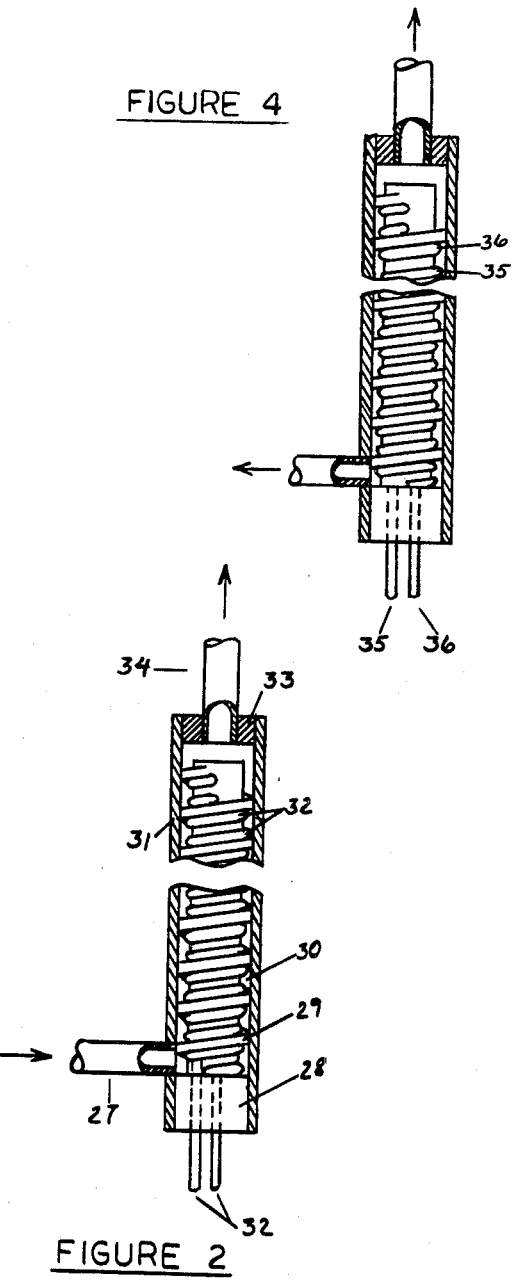
FIGURE 4
FIGURE 2
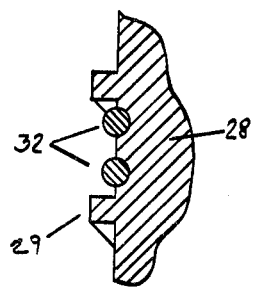
FIGURE 3
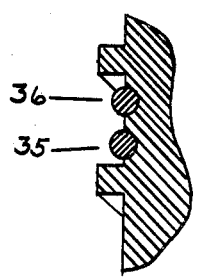
FIGURE 5

ELECTROLYTIC HYGROMETER IMPROVEMENT

DESCRIPTION

The electrolytic hygrometer was invented by Keidel, U.S. Pat. No. 2,830,945, and in his invention an electrolytic cell having a helically wound pair of platinum wires is used in the inner element with coating of an eletrolytically conducting material such as phosphorous pentoxide and with an insulating sleeve. The present invention is intended to improve a part of that invention such, for example, as was done in the Reeves, U.S. Pat. No. 3,223,609, wherein advantages were obtained by substituting rhodium for platinum wire in the helical pair of the cell. The discussion herein uses the expression precious metals to refer to the costly material above or to that of other such material that is relatively expensive. In the helically wound pairs of the cell element above it was of no significance to say that this wire of the pair shall be connected to a positive potential and that wire of the pair to a negative potential since the two wires were of the same material. It is a purpose of the present invention to make the electrolytical cell with the standard features of those above, such as the electrolytically conducting hygroscopic coating, with one of the helically wound pair to be of a precious metal, having circuit means that determine that its potential will be positive, a preferred metal being platinum, and with the other wire of the helically wound pair having circuit means that determine that its potential shall be negative. Thus it is a purpose of this invention that the negative wire of the helical pair shall be either the precious metal rhodium or a less costly metal such as tantalum, tungsten, or possibly nickel.

BRIEF DESCRIPTION OF THE DRAWINGS

FIG. 1 depicts a prior art system comprising a hygrometer in combination with a circuit therefor;

FIG. 2 shows a cross section of the structure of the hygrometer of FIG. 1;

FIG. 3 shows a closeup view of a portion of the hygrometer of FIG. 2;

FIG. 4 shows a cross section of the hygrometer of the present invention;

And FIG. 5 shows a closeup view of a portion of the hygrometer of FIG. 4.

The aims of the present invention will be made clearer by referring to the figures. FIGS. 1, 2, and 3 are essentially from the Keidel patent. Thus in FIG. 1, the tubing 1 carries a stream of gas from a sampling point with an adjustable bypass at 2 while a sample for measurement passes through tubing 3 to the electrolytic cell 4 then through the flow regulator 5 with its flow control means 6 set to give a standard flow of the sample as metered at flowmeter 7 with subsequent venting at 8. Two leads 9 and 10 make connection to the electrolytic cell 4 with its current metered by meter 11 with resistors 12, 13, 14, 15, 16, and 17 selected to give appropriate range selection in conjunction with the range switch 18 and its ganged positions 19, 20, 21, 22, and 23. Output for recording is obtained from potentiometer arm 24 at potentiometer 25 with resistor 26 selected as required. FIG. 2 shows a closer view of the cell makeup with inlet 27, outer shell 31, insulated plug 28, for the ends of the helical pair, shown as 32, output plug 33 and output tubing 34. FIG. 3 shows a closeup sectional view of a part of the cell of FIG. 2 and the wires 32 are seen, these being generally of diameter about 0.005", with separations, center to center, of the same magnitude. It is noted here that the leads 9 and 10 of FIG. 1 connect to the leads 32 of FIG. 2 in indiscriminate fashion since in this cell the helical pair consists of the same wire. The wires are shown here as supported on the insulated form 27 while in current practice, these are inside an insulating sheath which is then sealed in the outer casing 31. The gas flow is along the axis of the phosphorous pentoxide coated helical pairs. Also in practice the leads 32, or 35 and 36 are carried through the casing 31 while the gas inlet tube 27 is axial. In FIG. 4 the cell construction of the present invention is shown and wires 35 and 36 of the helical pair have different numbers since they are of different materials. The same distinction is carried into FIG. 5 and it is noted that with the cell of the present invention used as 4 in FIG. 1 and with the preferred precious metal as platinum, the terminal lead 10 of FIG. 1 connects to the terminal, say 35, which is say the platinum connection, while the second helical wire connects to 9. Thus if this wire is the precious metal rhodium, it connects to the negative terminal lead 9 of FIG. 1 and the same applies to the second helical wire when it is tantalum, tungsten or some other non-precious metals.

The connections for the precious metals noted above can be viewed as preferred while those for the non-precious metals such as tantalum and tungsten are mandatory. Thus platinum is found to behave better with oxygen than does rhodium while rhodium behaves better with hydrogen than does platinum. Behaving better here has the significance that there is greater catalytic recombination of hydrogen and oxygen in an oxygen stream with a rhodium cell than with a platinum cell while the reverse is true when the stream is one of hydrogen gas. In the present invention these empirical observations are extended to the selection of the individual wires. Where one wire of the helical pair is a non-precious metal, the electrolytic cell has been found to give unsatisfactory operation when that wire is positive. Operation with tantalum as the negative wire and a positive precious metal gave exceptional performance with many thousands of ppm-hours of operation at a moisture level averaging about 500 ppm/v. This compared favorably with that obtained with cells having two like precious metal wires in the helical pair. A cell with type 316 stainless steel was unsuccessful while the cell with one nickel wire got performance reports which were inconclusive but not necessarily negative.

The cost of tantalum or tungsten is a very small fraction of that of the precious metals so that, for instance, instead of purchasing x spools of platinum or rhodium at so many thousands of dollars, it becomes possible to cut these figures essentially in half by the use of the present invention. Equally well it is a much simpler problem to stock something whose price per pound is comparable to or significantly less than the price per ounce of the precious metal.

It is clear from what has been said that whereas in the cells with the same wire used in the helical pair it was not necessary to identify the terminal connections of the wires, the present invention requires that these be identified.

What is claimed is:

1. An electrolytic cell comprising an insulating outer casing and within that casing an inner element having a helical pair of wires of different material which are spaced from each other but in contact with a hygroscopic material which is electrically conducting only when wet, one of the wires being an anode selected from the class consisting of platinum and rhodium and the other being a cathode of tantalum.

2. An electrolytic cell comprising an insulating outer casing and within that casing an inner element having a helical pair of wires of different materials which are spaced from each other but in contact with a hygroscopic material which is electrically conducting only when wet, one of the wires being an anode selected from the class consisting of platinum and rhodium and the other being a cathode of tantalum, said wires having terminal connections which are independently identifiable, said element being sealed in said outer casing and said outer casing having connection means for passing gas through said element.

3. An electrolytic cell comprising an insulating outer casing and within that casing an inner element having a helical pair of wires of different materials which are spaced from each other but in contact with a hygroscopic material which is electrically conducting only when wet, one of the wires being an anode selected from the class consisting of platinum and rhodium and the other being a cathode of tantalum, said wires having terminal connections which are independently identifiable, said element being sealed in said outer casing and said outer casing having connection means for passing gas through said element, said terminal connections being continued through said outer casing.

4. An electrolytic cell of claim 3, which includes a means for regulating the rate at which gas flows through said element of said cell.

5. An electrolytic cell with gas regulating means of claim 4 which includes a voltage supply means for said cell.

6. An electrolytic cell with gas regulating means and voltage supply means of claim 5, which includes a means for measuring the current passing between the terminals of said cell.

* * * * *